(12) United States Patent
Foreman et al.

(10) Patent No.: US 7,748,529 B2
(45) Date of Patent: Jul. 6, 2010

(54) SURGICAL INSTRUMENT CASE

(75) Inventors: Chuck Foreman, Warsaw, IN (US); Kraig Allen, Warsaw, IN (US); John Conley, Claypool, IN (US); Dennis Brown, Warsaw, IN (US)

(73) Assignee: Symmetry Medical, Inc, Warsaw, IN (US)

( * ) Notice: Subject to any disclaimer, the term of this patent is extended or adjusted under 35 U.S.C. 154(b) by 698 days.

(21) Appl. No.: 11/376,812

(22) Filed: Mar. 16, 2006

(65) Prior Publication Data

US 2006/0213794 A1  Sep. 28, 2006

Related U.S. Application Data

(60) Provisional application No. 60/662,288, filed on Mar. 16, 2005.

(51) Int. Cl.
*B65D 83/10* (2006.01)
(52) U.S. Cl. .................... 206/370; 220/23.88
(58) Field of Classification Search ............... 206/370, 206/363, 499, 505, 368, 369; 220/23.83, 220/23.88, 23.87
See application file for complete search history.

(56) References Cited

U.S. PATENT DOCUMENTS

| 3,606,893 | A | * | 9/1971 | Verberg | 131/232 |
| 4,024,590 | A | * | 5/1977 | Wendt | 4/628 |
| 4,328,902 | A | * | 5/1982 | North | 220/23.4 |
| 4,717,024 | A | * | 1/1988 | Djezovic | 206/581 |
| 4,854,475 | A | | 8/1989 | Riihimaki et al. | 220/337 |
| 5,092,480 | A | * | 3/1992 | Waterston | 220/23.4 |
| 5,174,453 | A | | 12/1992 | Stoeffler | 206/570 |
| 5,297,674 | A | * | 3/1994 | Birutis et al. | 206/214 |
| 5,433,929 | A | | 7/1995 | Riihimaki et al. | 422/297 |
| 5,540,901 | A | | 7/1996 | Riley | 422/300 |
| 6,331,280 | B1 | | 12/2001 | Wood | 422/300 |
| 6,368,565 | B1 | | 4/2002 | Michaelson et al. | 422/300 |
| 6,534,000 | B1 | | 3/2003 | Michaelson et al. | 422/20 |
| 6,634,499 | B2 | | 10/2003 | Allen et al. | 206/370 |
| 6,866,147 | B2 | | 3/2005 | Barwick | 206/363 |
| 6,874,634 | B2 | | 4/2005 | Riley | 206/439 |
| 2004/0129595 | A1 | | 7/2004 | Dane et al. | 206/503 |

* cited by examiner

*Primary Examiner*—Jacob K Ackun, Jr.
(74) *Attorney, Agent, or Firm*—Taylor & Aust, P.C.

(57) ABSTRACT

A surgical instrument case which includes a primary case which is substantially rectangular and has a pair of opposite side walls, a pair of opposite end walls and a bottom wall. A secondary case fits within the primary case, and the secondary case has at least one attachment element on an outside surface of the secondary case. The at least one attachment element is configured for connecting to at least one of the side walls and the end walls when the secondary case is mounted on an outside of at least one of the opposite side walls and the opposite end walls.

15 Claims, 5 Drawing Sheets

SURGICAL INSTRUMENT CASE

CROSS REFERENCE TO RELATED APPLICATIONS

This is a non-provisional application based upon U.S. provisional patent application Ser. No. 60/662,288, entitled "SURGICAL INSTRUMENT CASE", filed Mar. 16, 2005.

BACKGROUND OF THE INVENTION

1. Field of the Invention

The present invention relates to surgical instrument cases, and, more particularly, to orthopaedic surgical instrument cases.

2. Description of the Related Art

Advances in the surgical arts, in particular the orthopaedic surgical arts, are often times accompanied by advances in surgical instruments associated with a particular procedure. Such advances sometimes produce more complex instrument sets with more numerous individual instruments. It is necessary for surgical instruments to be well organized, and visually available at a glance, when in use in an operating room in order to facilitate the efficient implementation of a surgical procedure. At the same time, operating rooms have limited table space available for surgical instrument cases. Additionally, such cases are typically used to hold the instruments during sterilization after surgical use, after which the cases may be enclosed in a sterile wrap.

In order to save space on an operating room backtable, and aid in the organization of surgical instruments, surgical instrument cases are known which add trays to the cases through hinged extension arms, similar to a tackle box. However, such a solution is relatively expensive to manufacture and can be damaged easily through rough handling, as such handling can torque and bend the arms thereby rendering the arms, and therefore the case, unusable.

A modular sterilization tray system for medical instruments is known which includes a rigid, substantially rectangular case having a pair of opposite side walls, a pair of opposite end walls and a bottom wall. A plurality of vertical columns of vertically spaced apart uniform size holes are formed in the case side walls and end walls. Also, one or more substantially rectilinear instrument trays are provided for placement in the case, the length and width dimensions of each of the trays being directly related to the spacing of the columns of holes in the case side and end walls such that one or more trays may be positioned within the case so as to be bracketed by selected columns of holes. The system also includes fixtures for positioning in selected holes of the bracketing columns of holes for fixing the position of one or more trays at a selected elevation in the case and fixation brackets for variously shaped instruments placed in the trays. Although this sterilization tray system includes instrument trays which are provided for placement in the case, there is no accommodation for the instrument trays except within the case, or on the surgical table, thereby taking up surgical table space when in use.

Another system is known which includes a modular sterilization tray system with a substantially rectangular case holding one or more trays. However, and as with the above described modular sterilization tray system, there is no accommodation for the instrument trays except within the case, or on the surgical table, thereby taking up surgical table space when in use.

A sterilization cassette and a sterilization method for sterilizing, storing, and dispensing dental instruments are known where the sterilization cassette includes a mounting bar and a locking bar for dental pliers of various types. A removable instrument tray is included, and a case with a front side which opens and hinges in two places, allowing the cassette to be arranged in horizontal and vertical configurations. Although this design has some versatility, when the front side is opened and the cassette is in the horizontal or vertical configurations, the footprint of the sterilization cassette is increased thereby taking up more space on a table or platform. Additionally, the hinges can be unreliable and/or difficult to clean and sterilize.

What is needed in the art is a surgical instrument case which saves space on an operating room backtable, aids in the organization of surgical instruments, is relatively inexpensive to manufacture, and is reliable in service even with rough handling.

SUMMARY OF THE INVENTION

The present invention provides a surgical instrument case including a primary case and at least one secondary case which can be mounted both within the primary case and on an outside of the primary case.

The invention comprises, in one form thereof, a surgical instrument case which includes a primary case which is substantially rectangular and has a pair of opposite side walls, a pair of opposite end walls and a bottom wall. A secondary case fits within the primary case, and the secondary case has at least one attachment element on an outside surface of the secondary case.

The at least one attachment element is configured for connecting to at least one of the side walls and the end walls when the secondary case is mounted on an outside of at least one of the opposite side walls and the opposite end walls.

The invention comprises, in another form thereof, a surgical instrument case assembly which includes at least one surgical instrument and a surgical instrument case which holds the at least one surgical instrument. The surgical instrument case includes a primary case which is substantially rectangular and has a pair of opposite side walls, a pair of opposite end walls and a bottom wall. A secondary case fits within the primary case, and the secondary case has at least one attachment element on an outside surface of the secondary case. The at least one attachment element is configured for connecting to at least one of the side walls and the end walls when the secondary case is mounted on an outside of at least one of the opposite side walls and the opposite end walls.

The invention comprises, in yet another form thereof, a surgical instrument case which includes a primary case with a substantially continuous perimeter wall connected to a bottom wall defining an enclosure therein. A secondary case fits within the enclosure, and the secondary case includes at least one attachment element on an outside surface of the secondary case. The at least one attachment element is configured for connecting to the perimeter wall when the secondary case is mounted on an outside of the perimeter wall.

The invention comprises, in yet another form thereof, a surgical instrument case assembly which includes at least one surgical instrument and a surgical instrument case holding the at least one surgical instrument. The surgical instrument case includes a primary case with a substantially continuous perimeter wall connected to a bottom wall defining an enclosure therein. A secondary case fits within the enclosure, and the secondary case includes at least one attachment element on an outside surface of the secondary case. The at least one attachment element is configured for connecting to the perimeter wall when the secondary case is mounted on an outside of the perimeter wall.

The invention comprises, in yet another form thereof, a method of using a surgical instrument case, which includes the steps of: providing a primary case being substantially rectangular and including a pair of opposite side walls, a pair of opposite end walls and a bottom wall; providing a secondary case fitting within the primary case, the secondary case including at least one attachment element on an outside surface of the secondary case; removing the secondary case from the primary case; and mounting the secondary case on an outside of at least one of the opposite side walls and the opposite end walls using at least one attachment element.

An advantage of the present invention is that usable space is added in the surgical room.

Another advantage is that the present invention has a compacted design while in or out of use.

Yet another advantage of the present invention is that it has a visually distinguishable layout.

Yet another advantage of the present invention is that usable space is added in the surgical case.

Yet another advantage of the present invention is that it has an ease of use.

Yet other advantages of the present invention is that it requires less table space in the operating room, storage room, sterilization chamber, etc.

Yet another advantage is the present invention is relatively inexpensive to manufacture.

Yet another advantage is the present invention is reliable in service even with rough handling.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplifications are not to be construed as limiting the scope of the invention in any manner.

DETAILED DESCRIPTION OF THE INVENTION

Figure 1:
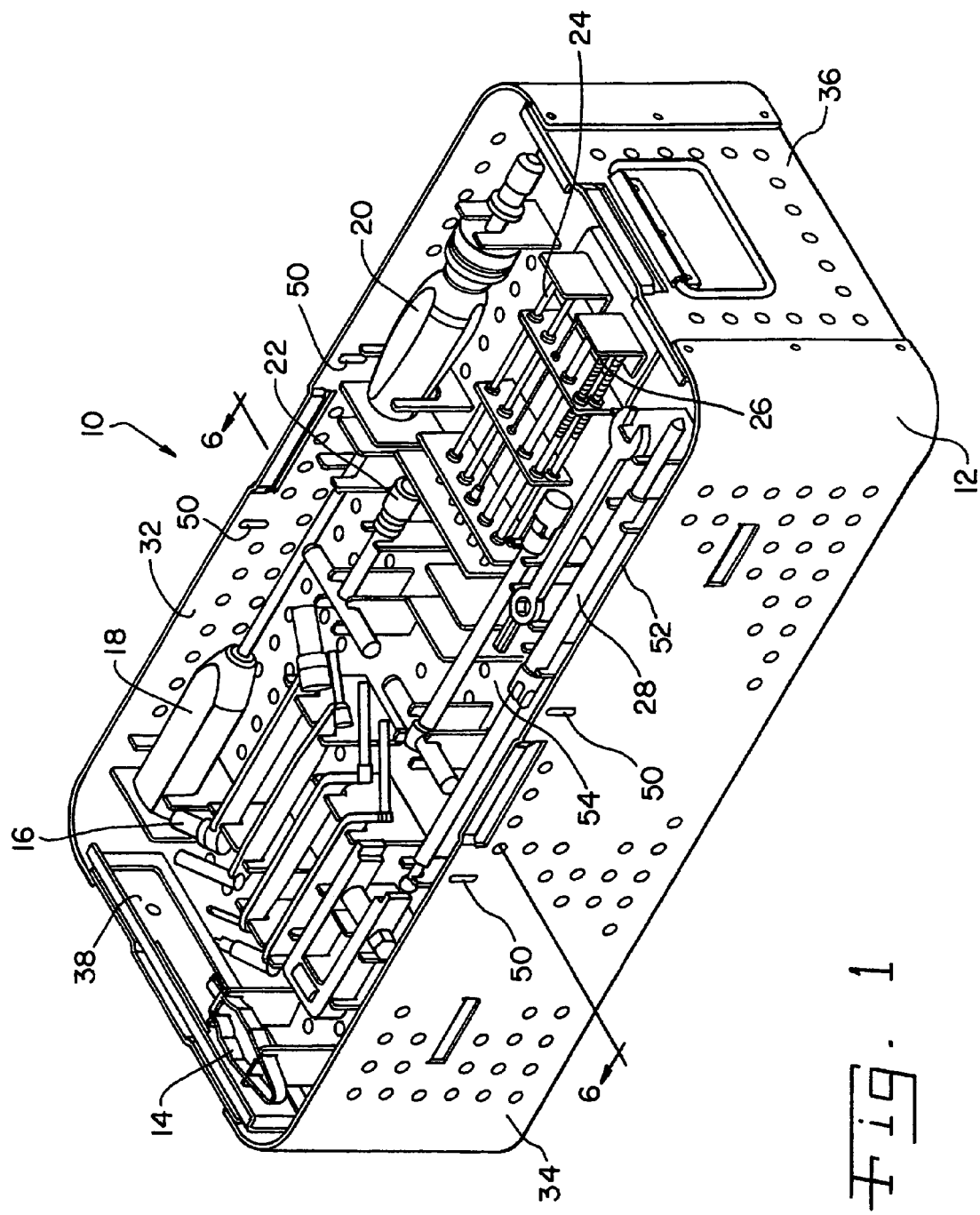
FIG. 1 is a perspective view of an embodiment of a surgical instrument case assembly including surgical instruments and a surgical instrument case according to the present invention.

Referring now to the drawings, and more particularly to FIG. 1, there is shown a surgical instrument case assembly 10 which generally includes surgical instrument case 12 and at least one surgical instrument.

For example, the surgical instruments can include, but are not limited to screw forceps 14, drill guide 16, screw driver 18, universal quick connect handle 20, universal quick connect driver 22, k-wires 24, taps 26 and depth gauge 28. In general the surgical instruments can include the instruments necessary to perform a given surgical procedure.

Figure 2:
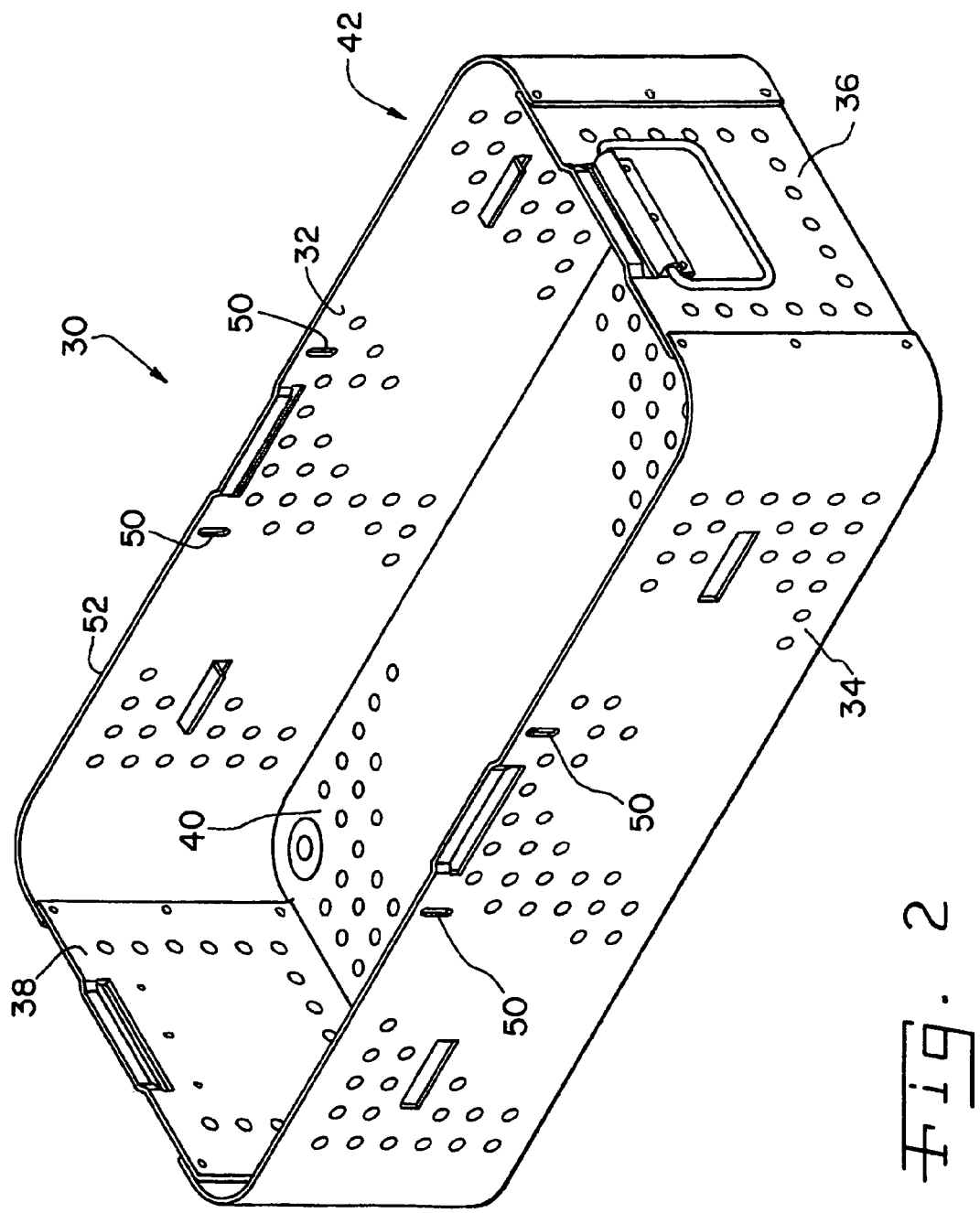
FIG. 2 is a perspective view of the primary case of FIG. 1.

Surgical instrument case 12 can include a primary case 30 (illustrated more clearly in FIG. 2) which is shown as substantially rectangular and includes a pair of opposite side walls 32, 34, a pair of opposite end walls 36, 38 and a bottom wall 40. Although primary case 30 in the embodiment shown is substantially rectangular, case 30 can include other shapes such as circular, elliptical, other curvatures or complex curvatures, square, polygonal, trapezoidal and other geometric shapes as are known, and/or some combination thereof. In general primary case 30 includes a substantially continuous perimeter wall, which in the embodiment shown is a combination of walls 32, 34, 36, 38, connected to bottom wall 40 and defining an enclosure 42 therein. Surgical instrument case 12 can additionally include a lid (not shown) covering primary case 30.

Figure 3:
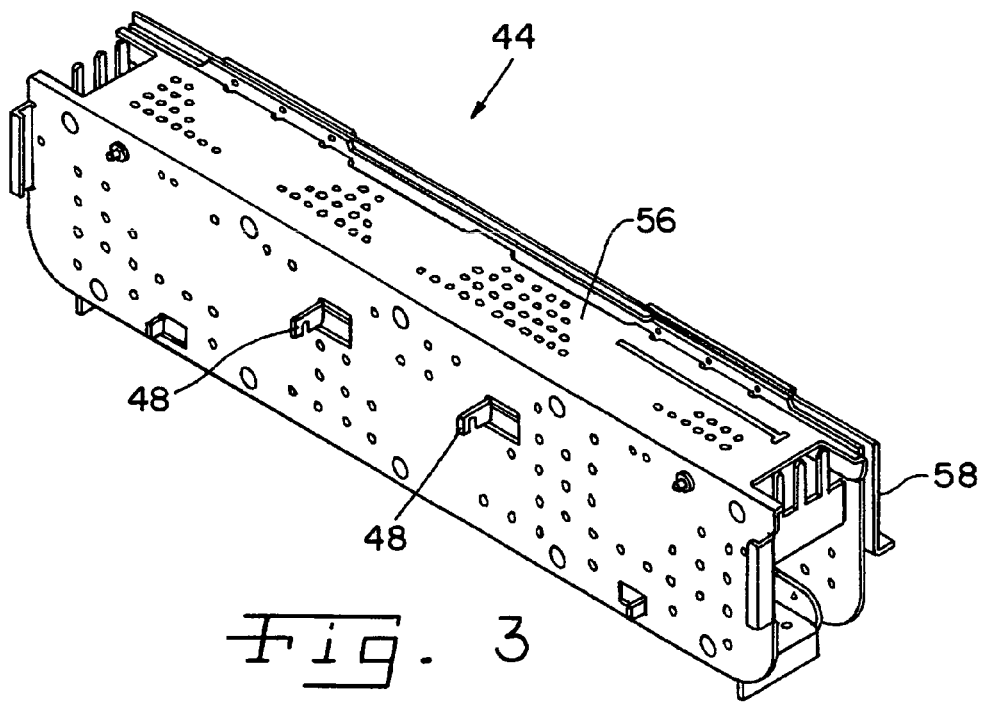
FIG. 3 is a perspective view of an embodiment of a secondary case of the surgical instrument case of FIG. 1, shown with its lid open.
Figure 4:
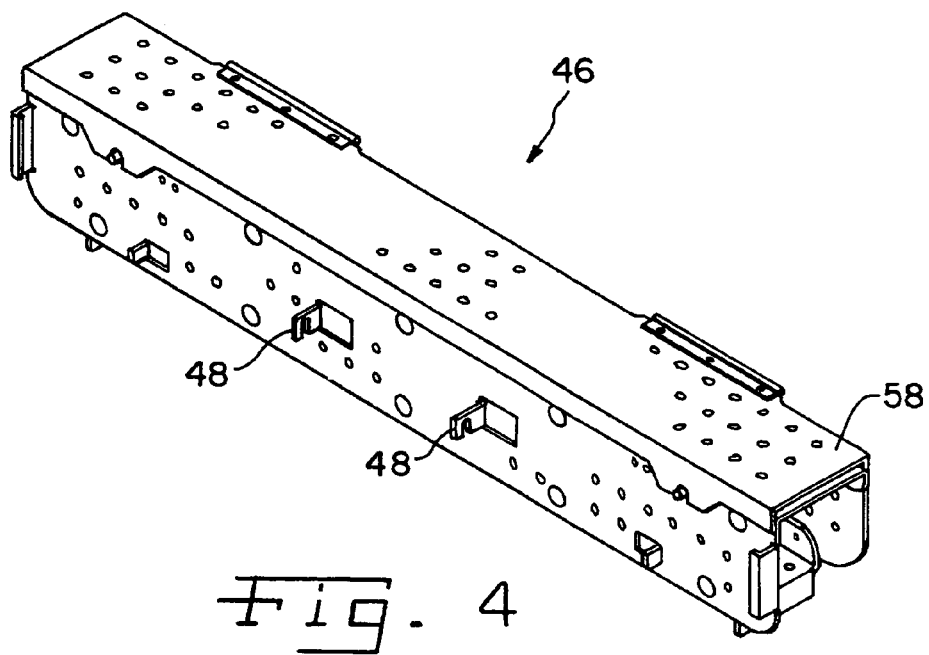
FIG. 4 is a perspective view of another embodiment of a secondary case of the surgical instrument case of FIG. 1, shown with its lid closed.
Figure 5:
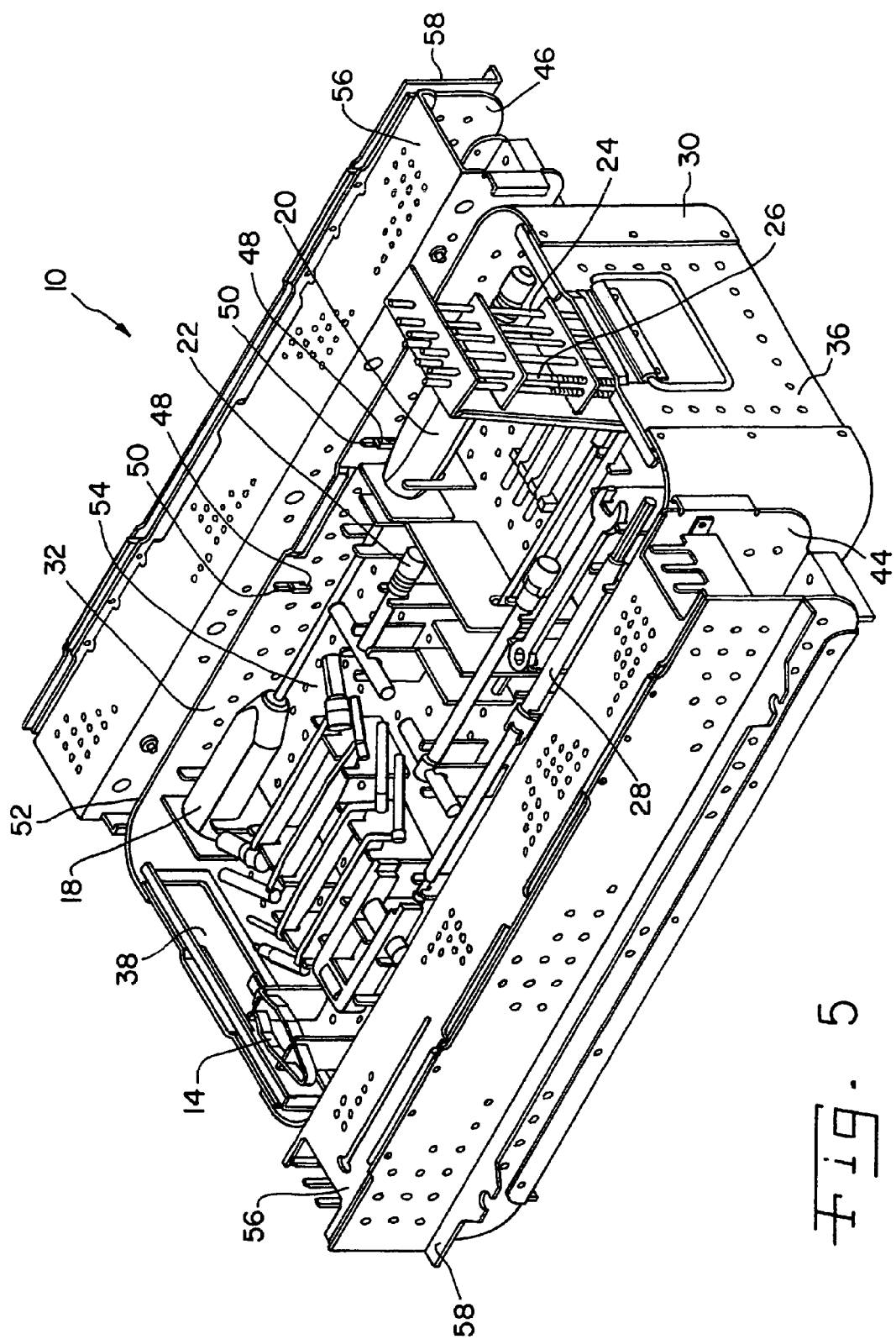
FIG. 5 is a perspective view of an expanded surgical instrument case assembly of FIG. 1, with the secondary cases mounted on the sides of the surgical instrument case.
Figure 6:
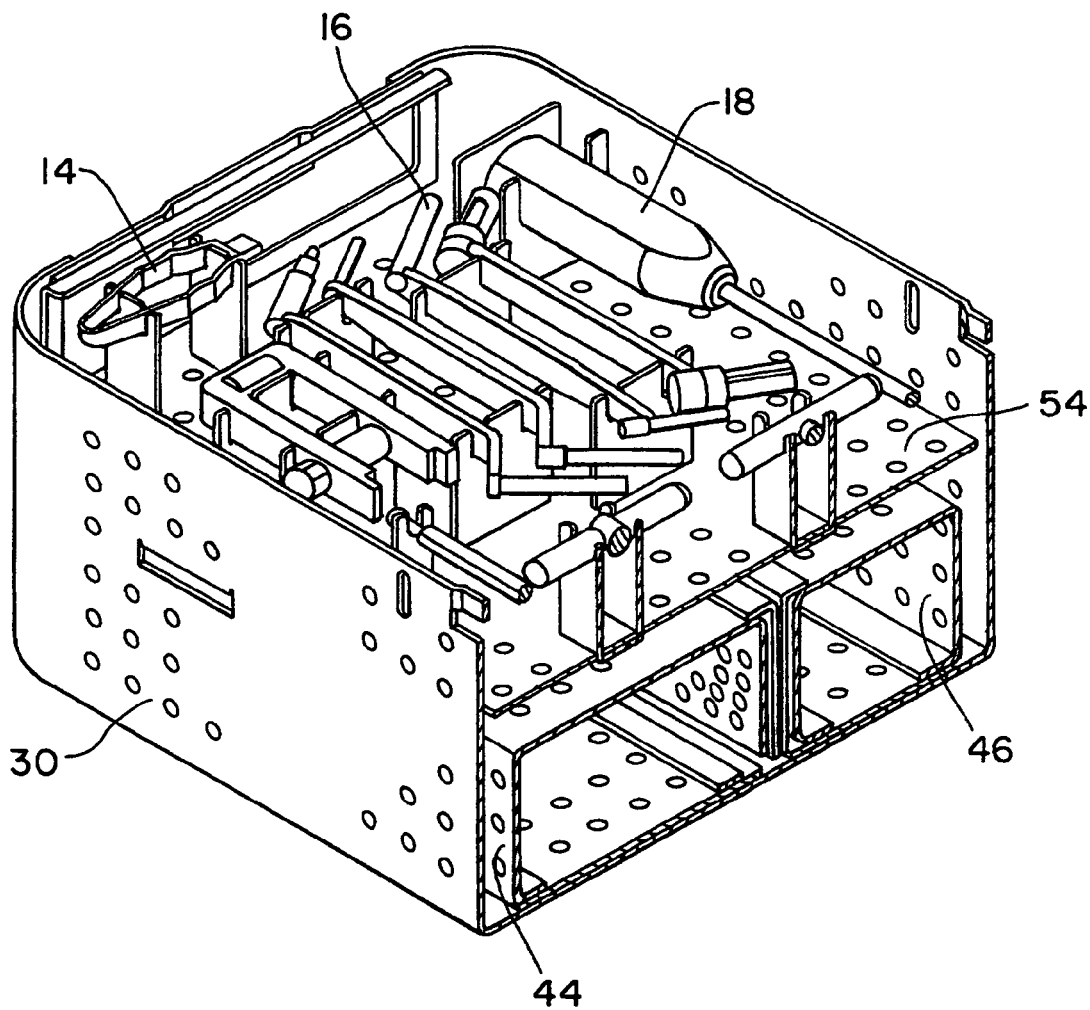
FIG. 6 is a perspective cross-sectional view taken along section line 6-6 in FIG. 1.

A secondary case 44, and in the embodiment shown, two secondary cases 44, 46, fit within primary case 30. Each of secondary cases 44, 46 include at least one attachment element 48 (best seen in FIGS. 3 and 4) on an outside surface of secondary case 44, 46. Attachment element 48 is configured for connecting to at least one of side walls 32, 34 and/or end walls 36, 38 when secondary case 44, 46 is mounted (FIG. 5) on an outside of at least one of walls 32, 34, 36, 38.

At least one of walls 32, 34, 36, 38 can include at least one slot 50, and attachment element(s) 48 are inserted into a corresponding slot 50. Attachment element(s) 48 can be in the form of a hook, as shown, or can include other shapes. Alternatively, attachment element(s) 48 can connect to an upper edge 52 of at least one of walls 32, 34, 36, 38.

Surgical instrument case 12 can further include a main tray 54 removably within primary case 30, where the secondary cases 44, 46 fit under main tray 54 when secondary cases 44, 46 are within primary case 30. Main tray 54 can include a variety of supports as shown to support respective surgical instruments. Secondary cases 44, 46 can include at least one of screw racks, drill caddies, and removable instrument holders as shown particularly at 56. Each of secondary cases 44, 46 can include a hinged cover 58 which is closed when secondary cases 44, 46 are stored within primary case 30.

Alternatively, secondary cases 44, 46 do not necessarily need to fit within primary case 30.

In use, the present invention discloses a method of using a surgical instrument case 12, comprising the steps of: providing a primary case 30 being substantially rectangular and including a pair of opposite side walls 32, 34, a pair of opposite end walls 36, 38 and a bottom wall 40; providing a secondary case 44 and/or 46 fitting within primary case 30, where secondary case 44 includes at least one attachment element 48 on an outside surface of secondary case 46; removing secondary case 44 and/or 46 from primary case 30; and mounting secondary case 46 on an outside of at least one of opposite side walls 32, 34 and/or opposite end walls 36, 38 using at least one attachment element 48.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A surgical instrument case, comprising:

a primary case being substantially rectangular and including a pair of opposite side walls, a pair of opposite end walls and a bottom wall;

a first secondary case fitting within said primary case, said secondary case including at least one attachment element on an outside surface of said secondary case, said at least one attachment element configured for connecting to at least one of said side walls and said end walls when said secondary case is mounted on an outside of at least one of said opposite side walls and said opposite end walls, the surgical instrument case being a sterilization case, said secondary case including a hinged cover;
a second secondary case fitting with said primary case; and
a main tray removably within said primary case, said first and second secondary cases fitting under said main tray when said first and second secondary cases are within said primary case.

2. The surgical instrument case of claim 1, wherein at least one of said opposite side walls and said opposite end walls include at least one slot, said at least one attachment element being inserted into a corresponding said at least one slot.

3. The surgical instrument case of claim 2, wherein at least one said attachment element is in a form of a hook.

4. The surgical instrument case of claim 1, wherein at least one said attachment element connects to an upper edge of at least one of said opposite side walls and said opposite end walls.

5. The surgical instrument case of claim 1, wherein at least one said attachment element is in a form of a hook.

6. The surgical instrument case of claim 1, wherein said first secondary case includes at least one of screw racks, drill caddies, and removable instrument holders.

7. A surgical instrument case assembly, comprising:
at least one surgical instrument;
a surgical instrument case holding said at least one surgical instrument, said surgical instrument case being a sterilization case and including:
  a primary case being substantially rectangular and including a pair of opposite side walls, a pair of opposite end walls and a bottom wall;
  a first secondary case fitting within said primary case, said secondary case including at least one attachment element on an outside surface of said secondary case, said at least one attachment element configured for connecting to at least one of said side walls and said end walls when said secondary case is mounted on an outside of at least one of said opposite side walls and said opposite end walls, said secondary case including a hinged cover;
a second secondary case fitting within said primary case; and
a main tray removably within said primary case, said first and second secondary cases fitting under said main tray when said first and second secondary cases are within said primary case.

8. The surgical instrument case assembly of claim 7, wherein at least one of said opposite side walls and said opposite end walls include at least one slot, said at least one attachment element being inserted into a corresponding said at least one slot.

9. The surgical instrument case assembly of claim 8, wherein at least one said attachment element is in a form of a hook.

10. The surgical instrument case assembly of claim 7, wherein at least one said attachment element connects to an upper edge of at least one of said opposite side walls and said opposite end walls.

11. The surgical instrument case assembly of claim 7, wherein at least one said attachment element is in a form of a hook.

12. The surgical instrument case assembly of claim 7, wherein said first secondary case includes at least one of screw racks, drill caddies, and removable instrument holders.

13. A surgical instrument case, comprising:
a primary case having a substantially continuous perimeter wall connected to a bottom wall defining an enclosure therein;
a first secondary case including at least one attachment element on an outside surface of said secondary case, said at least one attachment element configured for connecting to said perimeter wall when said secondary case is mounted on an outside of said perimeter wall, the surgical instrument case being a sterilization case, said secondary case including a hinged cover;
a second secondary case fitting within said primary case; and
a main tray removably within said primary case, said first and second secondary cases fitting within said enclosure under said main tray when said first and second secondary cases are within said primary case.

14. A surgical instrument case assembly, comprising:
at least one surgical instrument;
a surgical instrument case holding said at least one surgical instrument, said surgical instrument case being a sterilization case and including:
  a primary case having a substantially continuous perimeter wall connected to a bottom wall defining an enclosure therein;
  a first secondary case including at least one attachment element on an outside surface of said secondary case, said at least one attachment element configured for connecting to said perimeter wall when said secondary case is mounted on an outside of said perimeter wall, said secondary case including a hinged cover;
a second secondary case fitting within said primary case; and
a main tray removably within said primary case, said first and second secondary cases fitting within said enclosure under said main tray when said first and second secondary cases are within said primary case.

15. A method of using a surgical instrument case, comprising the steps of:
providing that the surgical instrument case is a sterilization case;
providing a primary case being substantially rectangular and including a pair of opposite side walls, a pair of opposite end walls and a bottom wall;
providing a first secondary case fitting within said primary case, said first secondary case including at least one attachment element on an outside surface of said first secondary case, said first secondary case including a hinged cover;
providing a second secondary case fitting within said primary case;
providing a main tray removably within said primary case;
removing said first secondary case from said primary case;
mounting said first secondary case on an outside of at least one of said opposite side walls and said opposite end walls using at least one attachment element; and
fitting said first and second secondary cases under said main tray when said first and second secondary cases are within said primary case.

* * * * *